US011369286B2

(12) United States Patent
Janik et al.

(10) Patent No.: US 11,369,286 B2
(45) Date of Patent: Jun. 28, 2022

(54) LOW CYANOSIS OBSERVATION INDEX LUMINAIRE

(71) Applicant: SIGNIFY HOLDING B.V., Eindhoven (NL)

(72) Inventors: Raymond George Janik, Fayetteville, GA (US); Russell Scott Trask, Sharpsburg, GA (US)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 17/151,549

(22) Filed: Jan. 18, 2021

(65) Prior Publication Data

US 2021/0219868 A1 Jul. 22, 2021

Related U.S. Application Data

(60) Provisional application No. 62/963,966, filed on Jan. 21, 2020.

(51) Int. Cl.
*A61B 5/103* (2006.01)
*H05B 45/20* (2020.01)
*A61B 5/00* (2006.01)

(52) U.S. Cl.
CPC .......... *A61B 5/1032* (2013.01); *A61B 5/0082* (2013.01); *H05B 45/20* (2020.01); *A61B 2562/0233* (2013.01)

(58) Field of Classification Search
CPC ... A61B 5/0082; A61B 5/1032; A61B 5/0088; A61B 2562/0233; H05B 45/20;

(Continued)

(56) References Cited

U.S. PATENT DOCUMENTS 9,609,715 B1 * 3/2017 Petluri .................... F21V 5/04
2011/0309773 A1 12/2011 Beers et al.
(Continued)

FOREIGN PATENT DOCUMENTS

AU 2011253704 A1 6/2012

OTHER PUBLICATIONS

Snjezana Soltic, et al., "Optimization of LED Lighting for Clinical Settings", Hindawi, Journal of Healthcare Engineering, vol. 2019, Article ID 5016013, 8 pages, https://doi.org/10.1155/2019/5016013.

*Primary Examiner* — Haissa Philogene
(74) *Attorney, Agent, or Firm* — Daniel J. Piotrowski (57) ABSTRACT

A lighting device, comprises a light source configured to provide a low Cyanosis Observation Index (COI) white light having a total flux, the light source comprising a first group of LEDs configured to provide a wide blue light, a second group of LEDs configured to provide a wide green light, and a third group of LEDs configured to provide a wide red light, wherein the low COI white light is a combination of at least the wide blue light, the wide green light, and the wide red light, wherein a current provided to the light source is distributed among the first group of LEDs, the second group of LEDs, and the third group of LEDs such that the wide blue light contributes 7 percent to 9 percent of the total flux, the wide green light contributes 62 percent to 76 percent of the total flux, and the wide red light contributes 20 percent to 26 percent of the total flux, and wherein a COI of the low COI white light is less than 1.

7 Claims, 8 Drawing Sheets

(58) Field of Classification Search
CPC ...... H05B 45/24; H05B 45/60; G09G 3/3413;
G09G 3/32; G09G 2380/08
See application file for complete search history.

(56) References Cited

U.S. PATENT DOCUMENTS

| | | | |
|---|---|---|---|
| 2014/0301062 A1* | 10/2014 | David | F21V 3/00 362/84 |
| 2017/0368210 A1 | 12/2017 | David et al. | |
| 2019/0254142 A1* | 8/2019 | Petluri | H05B 45/60 |
| 2019/0267356 A1* | 8/2019 | Soler | H05B 45/20 |
| 2020/0068674 A1 | 2/2020 | Petluri et al. | |

* cited by examiner

LOW CYANOSIS OBSERVATION INDEX LUMINAIRE

CROSS REFERENCE TO RELATED APPLICATIONS

This patent application claims the priority benefit of U.S. Application Ser. No. 62/963,966, filed Jan. 21, 2020, the contents of which are herein incorporated by reference.

TECHNICAL FIELD

The present disclosure relates generally to lighting solutions, and more particularly to lights that improve observation of tissue redness.

BACKGROUND

Diagnosing medical conditions may sometimes rely on the detection and observation of the redness of living tissue. In some cases, a low quality light source may not adequately reveal the redness of tissue, and the problem may be exaggerated with dark tissue, organs or skin. For example, a skin reaction (e.g., a raised skin) resulting from an allergy test may be missed due to low quality lighting. In general, the diagnosis of medical conditions that can be made by observing the redness of tissue may be affected by the quality of the available light. One quality measure of a light source to render blood rich tissue is the Cyanosis Observation Index, (COI), which is an Australian standard (AS1680.2.5:1997). Thus, a solution that enables improved detection and observation of the deep red color of oxygenated blood may be desirable.

BRIEF DESCRIPTION OF THE FIGURES

According to the invention, a lighting device, comprises a light source configured to provide a low Cyanosis Observation Index (COI) white light having a total flux, the light source comprising a first group of LEDs configured to provide a wide blue light, a second group of LEDs configured to provide a wide green light, and a third group of LEDs configured to provide a wide red light, wherein the low COI white light is a combination of at least the wide blue light, the wide green light, and the wide red light, wherein a current provided to the light source is distributed among the first group of LEDs, the second group of LEDs, and the third group of LEDs such that the wide blue light contributes 7 percent to 9 percent of the total flux, the wide green light contributes 62 percent to 76 percent of the total flux, and the wide red light contributes 20 percent to 26 percent of the total flux, and wherein a COI of the low COI white light is less than 1.

The proposed invention provides a high-quality light source, tuned for high rendering of oxygenated blood in living tissue, and having a relative high color rendering index.

Embodiments of the lighting device are provided in de dependent claims.

Reference will now be made to the accompanying drawings, which are not necessarily drawn to scale, and wherein.

The drawings illustrate only example embodiments and are therefore not to be considered limiting in scope. The elements and features shown in the drawings are not necessarily to scale, emphasis instead being placed upon clearly illustrating the principles of the example embodiments. Additionally, certain dimensions or placements may be exaggerated to help visually convey such principles. In the drawings, reference numerals designate like or corresponding, but not necessarily identical, elements.

DETAILED DESCRIPTION OF THE EXAMPLE EMBODIMENTS

In the following paragraphs, example embodiments will be described in further detail with reference to the figures. In the description, well known components, methods, and/or processing techniques are omitted or briefly described. Furthermore, reference to various feature(s) of the embodiments is not to suggest that all embodiments must include the referenced feature(s).

Figure 1:
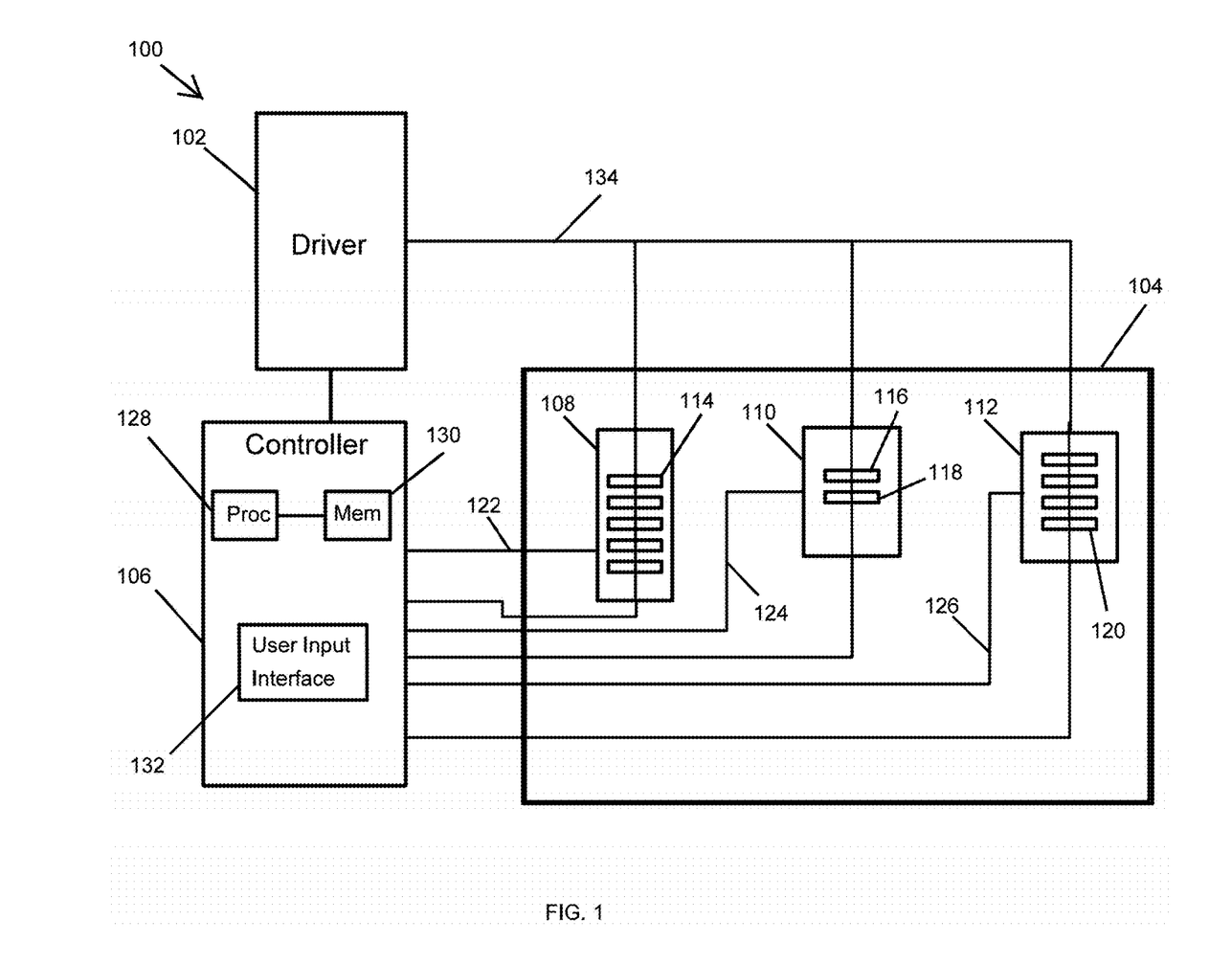
FIG. 1 illustrates a lighting device including a light source that produces a white light having a low Cyanosis Observation Index (COI) according to an example embodiment.

FIG. 1 illustrates a lighting device 100 (e.g., a lighting fixture) including a light source 104 that produces a white light having a low Cyanosis Observation Index (COI) according to an example embodiment. In some example embodiments, the lighting device 100 includes a driver 102, a controller 106, and a light source 104. The driver 102 may provide a current to the light source 104 via a connection 134 (e.g., one or more electrical wires or traces). The controller 106 may control the driver 102 to control the total amount of current provided to the light source 104. The current from the driver 102 may be distributed among the LED groups 108, 110, 112 of the light source 102. The controller 106 may control the distribution of the current among the LED groups 108, 110, 112 based on control signals provided to the LED groups 108, 110, 112 via electrical connections 122, 124, 126 (e.g., wires or traces). The controller 106 may determine the amount of current flowing through the individual LED groups 108, 110, 112 based on respective signals indicative of the respective current amounts as can be readily understood by those of ordinary skill in the art with the benefit of this disclosure.

In some example embodiments, the controller 106 may control the amount of current provided to the light source 104, for example, based on a default configuration or a user input provided via a user input interface 132. The user input interface 132 may receive user input wirelessly, via a wired connection, or via a direct user input. The controller 106 may also include a microcontroller 128, a memory device 130, and other components such as one or more analog-to-digital converters, one or more digital-to-analog converters, and other components as can be readily understood by those of ordinary skill in the art with the benefit of this disclosure. For example, the microcontroller 128 may execute software code stored in a memory device 130 to perform some of the operations described herein with respect to the controller 106 as can be understood by those of ordinary skill in the art with the benefit of this disclosure.

In some example embodiments, the light source 104 may include the first LED group 108, the second LED group 110, and the third LED group 112. The white light provided by the light source 104 may be a combination of the lights provided by the LED groups 108, 110, 112. Each LED group 108, 110, 112 may include one or more LED subgroups that each include one or more LEDs. The LED group 108 may emit a wide blue light, the LED group 110 may emit a wide green light, and the LED group 112 may emit a wide red light. Each of the wide blue light, wide green light, and the wide red light may be a combination of two of more lights.

In some example embodiments, the flux contribution of the wide blue light provided by the LED group 108, the wide green light provided by the LED group 110, and the wide red light provided by the LED group 112 to the total flux of the illumination white light provided by the light source 104 may be approximately 8%, 69%, and 23%. The flux contribution of the wide blue light may vary by approximately +/−1%, i.e., 7% to 9%. The 69% contribution of the wide green light may vary by approximately +/−7%, i.e., 62% to 76%. The 23% contribution of the wide red light may vary by approximately +/−3%, i.e., 20% to 26%. In some example embodiments, the correlated color temperature (CCT) of the white light provided by the light source 104 may be set or adjusted to approximately 4000 K. For example, the controller 106 may control the total amount of current provided by the driver 102 and/or the distribution of current among the LED groups 108, 110, 112 to turn on and off the light provided by the light source 104 and to control, for example, the dim level of the light, the color temperature of the light, etc.

In some example embodiments, the LED group 108 may include at least five LED subgroups including the LED subgroup 114. Each LED subgroup of the LED group 108 may include one or more LEDs and may emit a respective light that has a different color from the lights emitted by the other LED subgroups of the LED group 108. For example, the wide blue light provided by the LED group 108 may be a combination of at least a phosphor converted green light, a cyan light, a blue light, a royal red light, and a direct emission violet light. To illustrate, the phosphor converted green light may be emitted by a first LED subgroup of the LED group 108, the cyan light may be emitted by a second LED subgroup of the LED group 108, the blue light may be emitted by a third LED subgroup of the LED group 108, the royal red light may be emitted by a fourth LED subgroup of the LED group 108, the violet light may be emitted by a fifth LED subgroup of the first LED group 108.

In some example embodiments, the LED group 110 may include at least two LED subgroups including the LED subgroups 116, 118. The LED subgroup 116 of the LED group 110 may include one or more LEDs and may emit a light that has a different color from the light emitted by the LED subgroup 118 of the LED group 110. For example, the wide green light provided by the LED group 110 may be a combination of at least a cyan light and a phosphor converted green light. To illustrate, the cyan light may be emitted by the LED subgroup 116 of the LED group 110, and the phosphor converted green light may be emitted by the LED subgroup 118 of the LED group 110.

In some example embodiments, the LED group 112 may include at least four LED subgroups including the LED subgroup 120. Each LED subgroup of the LED group 112 may include one or more LEDs and may emit a respective light that has a different color from the lights emitted by the other LED subgroups of the LED group 112. For example, the wide red light provided by the LED group 112 may be a combination of at least a phosphor converted yellow light, a phosphor converted amber light, a phosphor converted red light, and a deep red light. To illustrate, the phosphor converted yellow light may be emitted by a first LED subgroup of the LED group 112, the phosphor converted amber light may be emitted by a second LED subgroup of the LED group 112, the phosphor converted red light may be emitted by a third LED subgroup of the LED group 112, the deep red light may be emitted by a fourth LED subgroup (e.g., the LED subgroup 120) of the LED group 112.

In some example embodiments, the contributions of the fluxes of the phosphor converted green light, the cyan light, the blue light, the royal red light, and the violet light to the wide blue light provided by the LED group 108 may be approximately 40%, 37%, 16%, 6.4%, and 0.6%, respectively, where each percentage contribution may vary by about 10%. The contributions of the fluxes of the cyan light and the phosphor converted green light to the wide green light provided by the LED group 110 may be approximately 70% and 30%, respectively, where each percentage contribution may vary by about 10%. The contributions of the fluxes of the phosphor converted yellow light, a phosphor converted amber light, a phosphor converted red light, and a deep red light to the wide red light provided by the LED group 112 may be approximately 54%, 28%, 12%, and 6%, respectively, where each percentage contribution may vary by about 10%.

In some example embodiments, the light provided by the lighting device 100, which is a combination of the lights provided by the LED groups 108, 110, 112, may have a relatively low Cyanosis Observation Index (COI). The COI is related to the bluish discoloration in skin and mucous membranes that indicates oxygen levels in the blood. The light provided by the lighting device 100 may have a COI of less than 1, which may result in high rendering of oxygenated blood in living tissue that may not be achieved by lights that have a higher COI. For example, the COI of the light may be approximately 0.1 or less at 4000 K CCT. The light may also have TM-30 Rf of 98, TM-30 Rg of 100, and CRI of 99. In some example embodiments, the CCT of the light may be between 3800 K and 4200 K while enabling high rendering of oxygenated blood in living tissue. For example, the CCT may be 4000 K. In some alternative embodiments, the CCT of the light may be adjusted in a range from below 3800 K to above 4200 K. Because of its relatively low COI of less than 1, the light provided by the lighting device 100 may be useful in detecting redness in skin tissue that may otherwise be missed when using lights that have a higher COI. In general, the light may enable a more reliable detection of cyanosis that may not be achieved using lights with higher COI. Some health related observations, such as observations of skin allergy response, skin disorder, etc., may also be more easily made using the light provided by the lighting device 100.

In some alternative embodiments, the components of the lighting device 100 may be coupled in a different configuration than shown without departing from the scope of this disclosure. In some alternative embodiments, some of the components may be integrated into a single component. In some alternative embodiments, the lighting device 100 may include more or fewer LED groups and some of the LED groups may include more or fewer LEDs than shown.

Figure 2:
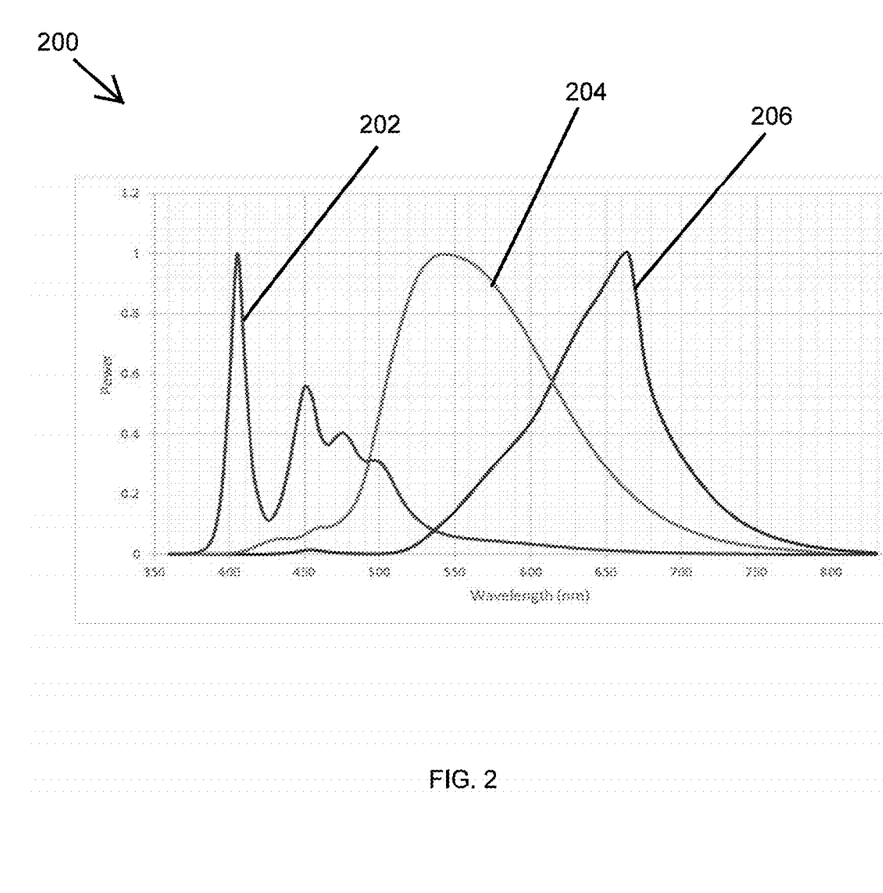
FIG. 2 illustrates spectral distributions of different lights produced by LED groups of the light source of the lighting device of FIG. 1 according to an example embodiment.

FIG. 2 illustrates spectral distributions of different lights produced by LED groups of the light source 104 of the lighting device 100 of FIG. 1 according to an example embodiment. Referring to FIGS. 1 and 2, the curve 202 may represent the spectral distribution of the wide blue light emitted by the LED group 108. The curve 204 may represent the spectral distribution of the wide green light emitted by the LED group 110. The curve 206 may represent the spectral distribution of the wide red light emitted by the LED group 112.

Figure 3:
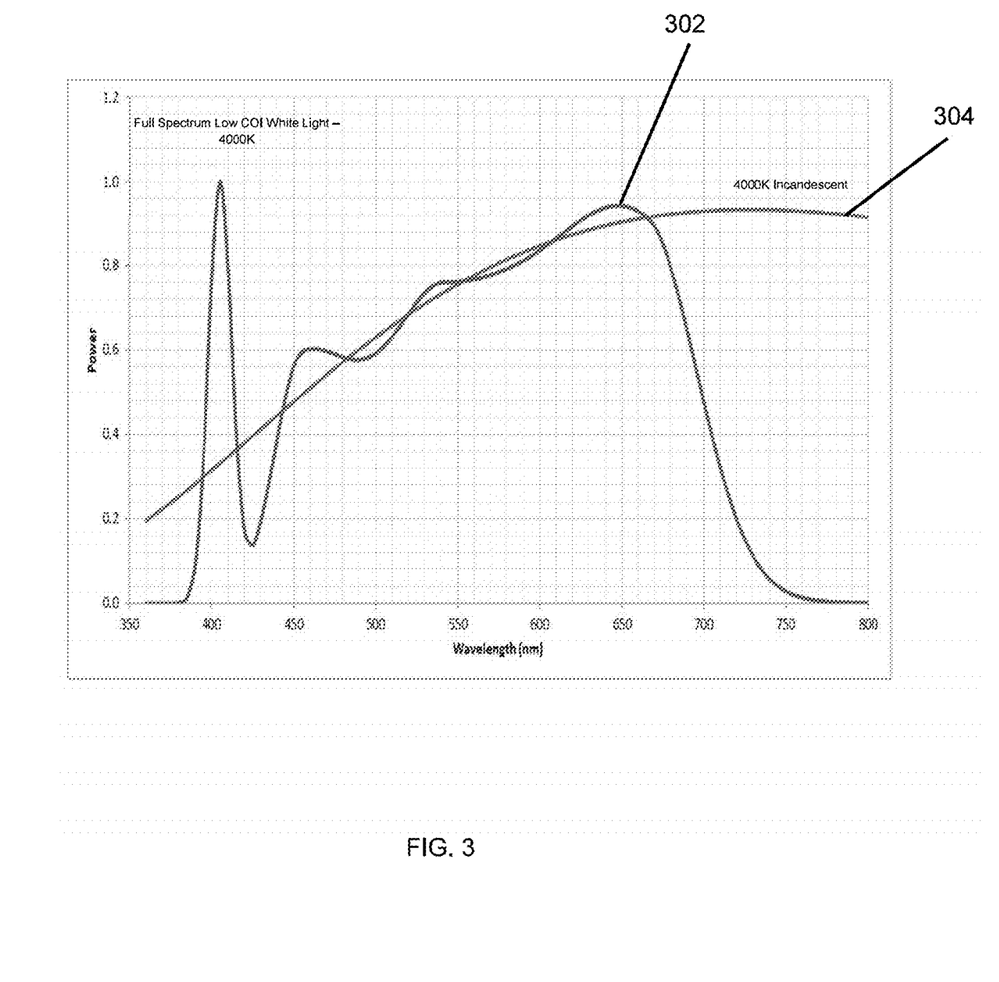
FIG. 3 illustrates a spectral distribution of the low COI white light produced by the lighting device of FIG. 1 and a spectral distribution of an incandescent light at a correlated color temperature (CCT) of 4000K according to an example embodiment.

FIG. 3 illustrates a spectral distribution of the low COI white light produced by the lighting device 100 of FIG. 1 and a spectral distribution of an incandescent light at a correlated color temperature (CCT) of 4000K according to an example embodiment. The spectral distribution of the low COI white light is represented by the curve 302, and the spectral distribution of the incandescent light is represented by the curve 304. For example, the spectral distribution of the low COI white light may be a combination of the spectral distributions of the wide blue light, the wide green light, and the wide red light shown in FIG. 2.

Figure 4:
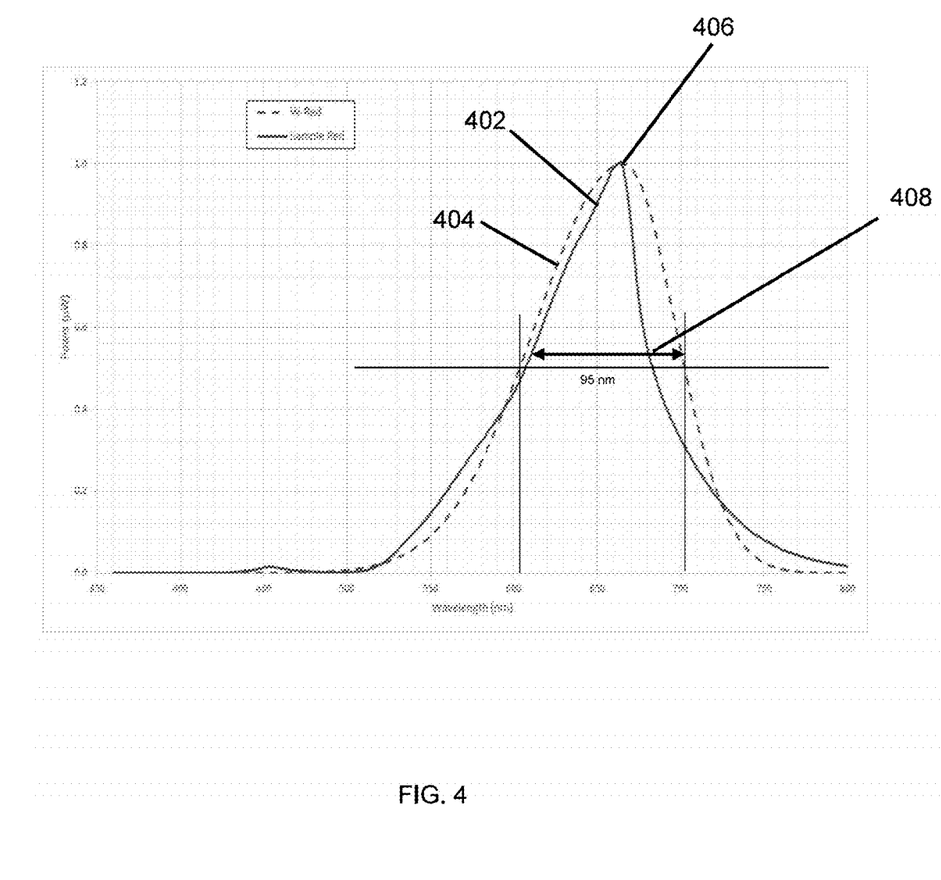
FIG. 4 illustrates a spectral distribution of a wide red light emitted by an LED group of the light source of the lighting device of FIG. 1 according to an example embodiment.

FIG. 4 illustrates a spectral distribution of a wide red light emitted by the LED group 112 of the light source 104 of the lighting device of FIG. 1 according to an example embodiment. The curve 402 may represent the spectral distribution of the wide red light provided by the LED group 112, and the curve 404 may represent a model spectral distribution of the wide red light generated using Equation 1.

$$P(\lambda) = \begin{cases} a \cdot e^{-\frac{1}{2}\left(\frac{\lambda-\lambda_0}{54}\right)^2} & \lambda < \lambda_0 \\ a \cdot e^{-\frac{1}{2}\left(\frac{\lambda-\lambda_0}{25}\right)^2} & \text{elsewhere} \end{cases} \quad \text{Equation 1}$$

The wavelength $\lambda_0$ at the peak 406 may vary between 650 nm and 680 nm (e.g., 666 nm). The full width at half maximum (FWHM) of the wide red light as determined based on the curve 404 may range between 65 nm and 130 nm. For example, the FWHM may be 95 nm as shown in FIG. 4.

Figure 5:
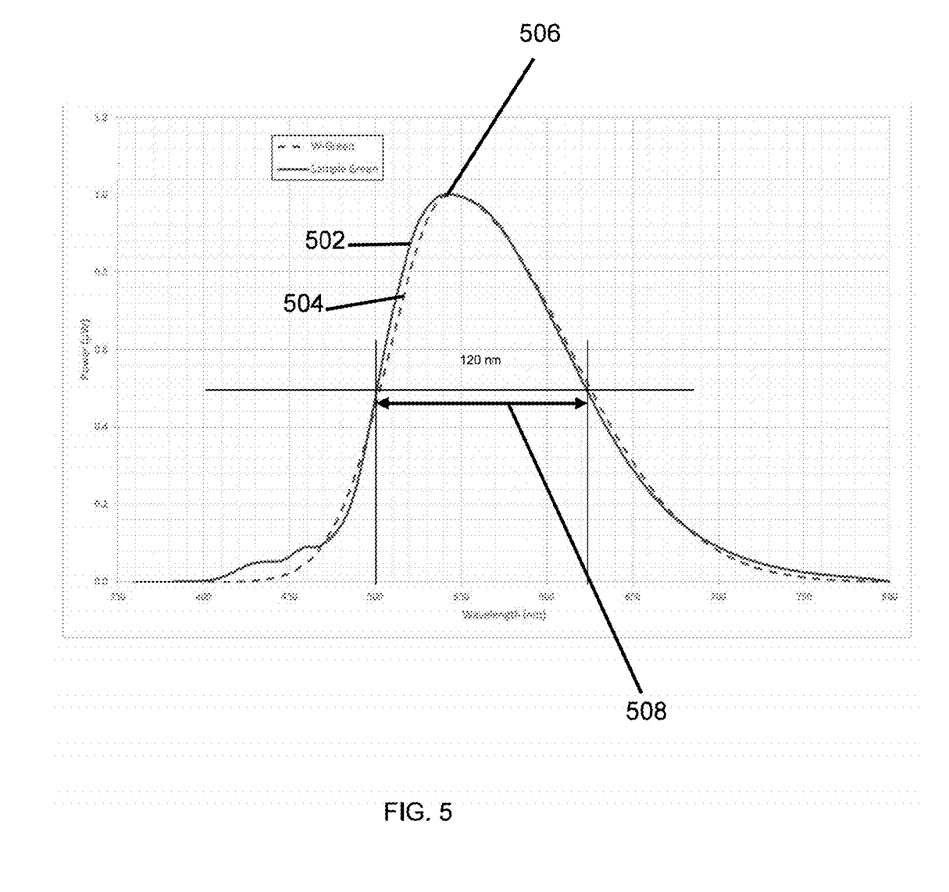
FIG. 5 illustrates a spectral distribution of a wide green light emitted by an LED group of the light source of the lighting device of FIG. 1 according to an example embodiment.

FIG. 5 illustrates a spectral distribution of a wide green light emitted by the LED group 110 of the light source 104 of the lighting device of FIG. 1 according to an example embodiment. The curve 502 may represent the spectral distribution of the wide green light provided by the LED group 110, and the curve 504 may represent a model spectral distribution of the wide green light generated using Equation 2.

$$P(\lambda) = \begin{cases} a \cdot e^{-\frac{1}{2}\left(\frac{\lambda-\lambda_0}{34}\right)^2} & \lambda < \lambda_0 \\ a \cdot e^{-\frac{1}{2}\left(\frac{\lambda-\lambda_0}{70}\right)^2} & \text{elsewhere} \end{cases} \quad \text{Equation 2}$$

The wavelength $\lambda_0$ at the peak 506 may vary between 537 nm and 555 nm (e.g., 543 nm). The full width at half maximum (FWHM) of the wide red light as determined based on the curve 504 may range between 100 nm and 150 nm. For example, the FWHM may be 12 nm as shown in FIG. 5.

Figure 6:
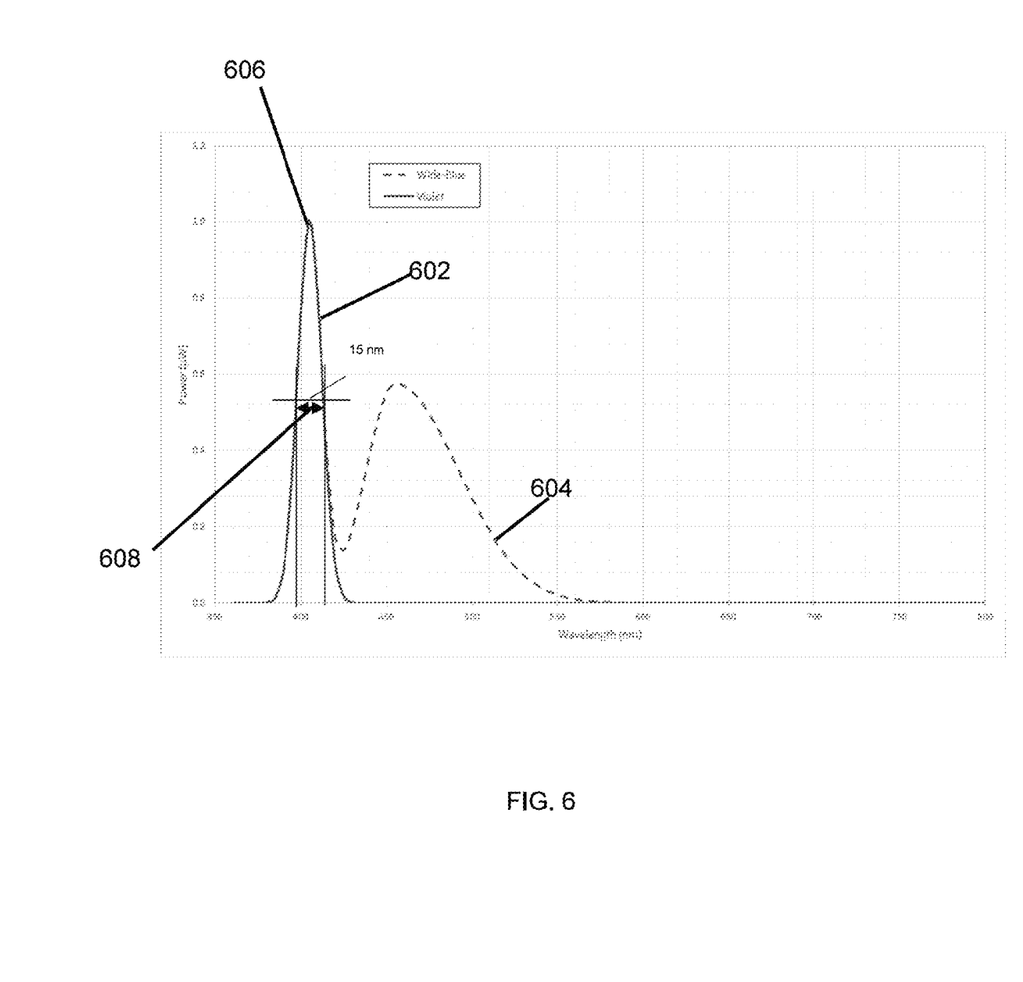
FIG. 6 illustrates a spectral distribution of a violet light component of a wide blue light emitted by an LED group of the light source of the lighting device of FIG. 1 according to an example embodiment.

FIG. 6 illustrates a spectral distribution of a violet light component of a wide blue light emitted by the LED group 108 of the light source 104 of the lighting device of FIG. 1 according to an example embodiment. For example, the wide blue light emitted may be dominated by two components: a direct emission violet light (i.e., violet light component) and a phosphor converted blue light (i.e., blue light component). The curve 602 may represent the spectral distribution of the violet light of the wide blue light provided by the LED group 108, and the curve 604 may represent a model spectral distribution of the violet light generated using Equation 3.

$$P(\lambda) = \begin{cases} a \cdot e^{-\frac{1}{2}\left(\frac{\lambda-\lambda_0}{7}\right)^2} & \lambda < \lambda_0 \\ a \cdot e^{-\frac{1}{2}\left(\frac{\lambda-\lambda_0}{7}\right)^2} & \text{elsewhere} \end{cases} \quad \text{Equation 3}$$

The wavelength $\lambda_0$ at the peak 606 may vary between 400 nm and 430 nm (e.g., 405 nm). The full width at half maximum (FWHM) of the wide red light as determined based on the curve 604 may range between 3 nm and 33 nm. For example, the FWHM may be 15 nm as shown in FIG. 6.

Figure 7:
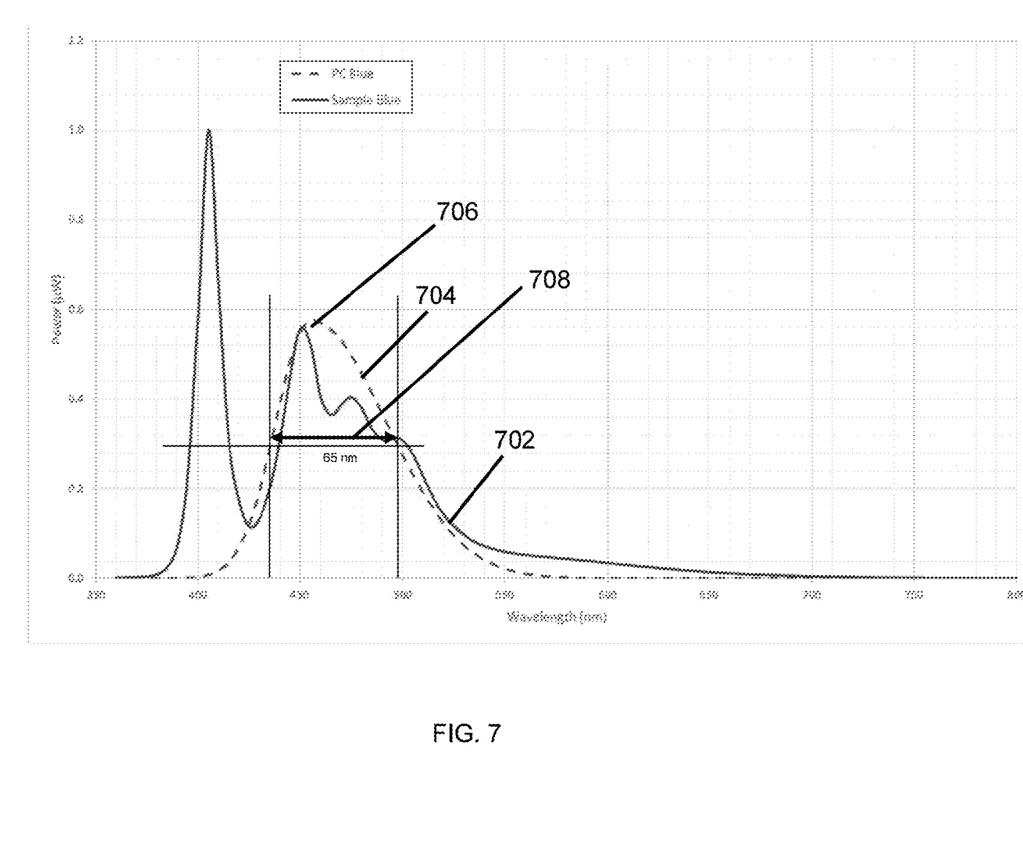
FIG. 7 illustrates a spectral distribution of a blue light component of a wide blue light emitted by the LED group of the light source of the lighting device of FIG. 1 according to an example embodiment.

FIG. 7 illustrates a spectral distribution of a blue light component of the wide blue light emitted by the LED group 108 of the light source 104 of the lighting device of FIG. 1 according to an example embodiment. As described above, the wide blue light emitted may be dominated by two components: the direct emission violet light (i.e., violet light component) and the phosphor converted blue light (i.e., blue light component). The curve 702 may represent the spectral distribution of the phosphor converted blue light of the wide blue light provided by the LED group 112, and the curve 704 may represent a model spectral distribution of the phosphor converted blue light generated using Equation 4.

$$P(\lambda) = \begin{cases} a \cdot e^{-\frac{1}{2}\left(\frac{\lambda-\lambda_0}{17}\right)^2} & \lambda < \lambda_0 \\ a \cdot e^{-\frac{1}{2}\left(\frac{\lambda-\lambda_0}{37}\right)^2} & \text{elsewhere} \end{cases} \quad \text{Equation 4}$$

The wavelength $\lambda_0$ at the peak 706 may vary between 445 nm and 465 nm (e.g., 455 nm). The full width at half maximum (FWHM) of the wide red light as determined based on the curve 704 may range between 45 nm and 85 nm. For example, the FWHM may be 65 nm as shown in FIG. 7.

Figure 8:
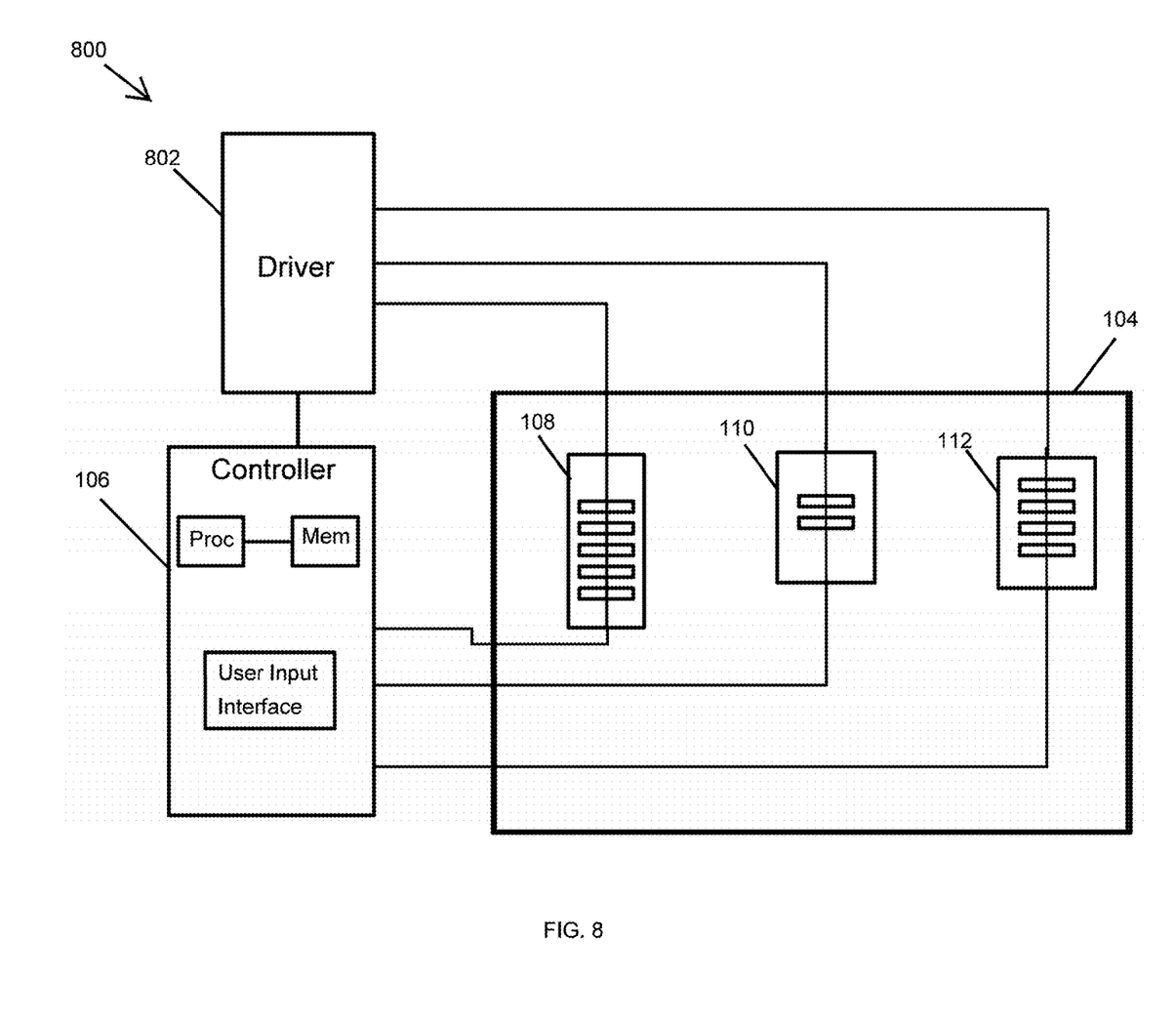
FIG. 8 illustrates a lighting device including a light source that produces a low COI white light according to another example embodiment.

FIG. 8 illustrates a lighting device 800 including the light source 104 that produces a low COI white light according to another example embodiment.

Although particular embodiments have been described herein in detail, the descriptions are by way of example. The features of the example embodiments described herein are representative and, in alternative embodiments, certain features, elements, and/or steps may be added or omitted. Additionally, modifications to aspects of the example embodiments described herein may be made by those skilled in the art without departing from the spirit and scope of the following claims, the scope of which are to be accorded the broadest interpretation so as to encompass modifications and equivalent structures.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention claimed is:

1. A lighting device, comprising:
a light source configured to provide a low Cyanosis Observation Index (COI) white light having a total flux, the light source comprising:
a first group of LEDs configured to provide a wide blue light;
a second group of LEDs configured to provide a wide green light; and
a third group of LEDs configured to provide a wide red light, wherein the low COI white light is a combination of at least the wide blue light, the wide green light, and the wide red light, wherein a current provided to the light source is distributed among the first group of LEDs, the second group of LEDs, and the third group of LEDs such that the wide blue light contributes 7 percent to 9 percent of the total flux, the wide green light contributes 62 percent to 76 percent of the total flux, and the wide red light contributes 20 percent to 26 percent of the total flux, and wherein a COI of the low COI white light is less than 1.

2. The lighting device of claim 1, wherein a wavelength of the wide red light is in the range of 650 nm to 680 nm.

3. The lighting device of claim 1, wherein a wavelength of the wide green light is in the range of 537 nm to 555 nm.

4. The lighting device of claim 1, wherein the wide blue light is a combination of at least a phosphor converted blue light and a direct emission violet light.

5. The lighting device of claim 4, wherein a wavelength of the phosphor converted blue light is in the range of 445 nm to 465 nm and wherein a wavelength of the direct emission violet light is in the range of 400 nm to 430 nm.

6. The lighting device of claim 5, wherein the wide blue light further includes a phosphor converted green light, a cyan light, and a royal blue light.

7. The lighting device of claim 1, wherein the COI of the low COI white light is less than 0.1.

* * * * *